(12) United States Patent
Gross et al.

(10) Patent No.: US 7,247,606 B2
(45) Date of Patent: Jul. 24, 2007

(54) BRANCHED REACTION PRODUCTS

(75) Inventors: Stephen F. Gross, Souderton, PA (US);
Norman Milstein, Cincinnati, OH (US)

(73) Assignee: Cognis Corporation, Ambler, PA (US)

( * ) Notice: Subject to any disclaimer, the term of this patent is extended or adjusted under 35 U.S.C. 154(b) by 0 days.

(21) Appl. No.: 10/265,004

(22) Filed: Oct. 4, 2002

(65) Prior Publication Data

US 2003/0162842 A1 Aug. 28, 2003

Related U.S. Application Data

(60) Provisional application No. 60/338,743, filed on Nov. 5, 2001.

(51) Int. Cl.
*B01F 17/46* (2006.01)
*B01D 19/04* (2006.01)
*C07C 217/04* (2006.01)
*C07C 217/28* (2006.01)
*C09D 11/00* (2006.01)
*C10M 173/00* (2006.01)
*C09K 3/00* (2006.01)

(52) U.S. Cl. .................. 508/462; 516/71; 516/129; 510/470; 510/499; 564/346; 564/501; 564/505; 106/31.43; 106/31.75; 524/243

(58) Field of Classification Search ............. 516/71, 516/129; 510/470, 499; 560/240, 250, 252; 564/346, 505, 501; 106/31.43, 31.75; 524/243; 508/562, 462

See application file for complete search history.

(56) References Cited

U.S. PATENT DOCUMENTS

| | | | | |
|---|---|---|---|---|
| 2,355,337 A | | 8/1944 | Spence ...................... 564/346 |
| 2,392,158 A | * | 1/1946 | Lacey et al. ................. 564/505 |
| 3,705,139 A | * | 12/1972 | Yamane et al. .............. 524/173 |
| 4,408,075 A | * | 10/1983 | Soula et al. ................. 564/474 |
| 4,417,048 A | * | 11/1983 | Soula et al. .................... 544/38 |
| 4,438,022 A | | 3/1984 | Campbell .................... 508/559 |
| 4,650,865 A | * | 3/1987 | Lange et al. ................. 564/505 |
| 4,719,044 A | | 1/1988 | Piorr et al. .................. 516/129 |
| 4,744,923 A | | 5/1988 | Piorr et al. .................. 516/129 |
| 4,935,159 A | | 6/1990 | Schenker et al. ........... 510/499 |
| 5,114,428 A | | 5/1992 | Hoeffkes et al. ................ 8/405 |
| 5,389,134 A | * | 2/1995 | Breton et al. ............. 106/31.43 |
| 5,421,993 A | | 6/1995 | Hille et al. .................. 516/179 |
| 5,563,251 A | * | 10/1996 | Lachocki .................... 536/18.3 |
| 5,573,707 A | | 11/1996 | Cole et al. ................... 516/129 |
| 5,728,895 A | | 3/1998 | Wiggins et al. .............. 568/601 |
| 5,877,245 A | | 3/1999 | Wiggins et al. .............. 524/366 |
| 5,895,605 A | | 4/1999 | Gross et al. ................. 516/134 |
| 5,936,107 A | * | 8/1999 | Raths et al. ................. 554/149 |
| 5,962,749 A | * | 10/1999 | Parsons et al. ............. 568/621 |
| 6,002,049 A | | 12/1999 | Wiggins et al. .............. 568/601 |
| 6,110,977 A | | 8/2000 | Gross et al. ................... 516/74 |
| 6,437,185 B1 | * | 8/2002 | Walele et al. ................ 564/293 |
| 6,475,419 B1 | * | 11/2002 | Lagarden et al. ........... 564/297 |
| 6,532,973 B1 | * | 3/2003 | Gross et al. ................ 510/470 |
| 6,566,317 B2 | * | 5/2003 | Morris et al. ................ 510/470 |
| 6,627,776 B2 | * | 9/2003 | Walele et al. ................ 564/505 |
| 2002/0103102 A1 | * | 8/2002 | Gross et al ................ 510/499 |
| 2003/0089150 A1 | * | 5/2003 | Markusch et al. ......... 71/64.07 |

FOREIGN PATENT DOCUMENTS

| | | | |
|---|---|---|---|
| AU | A-76411/96 | * | 6/1997 |
| WO | WO 99/29937 | * | 6/1999 |

* cited by examiner

*Primary Examiner*—Daniel S. Metzmaier
(74) *Attorney, Agent, or Firm*—John F. Daniels; Daniel S. Ortiz

(57) ABSTRACT

A compound of formula:

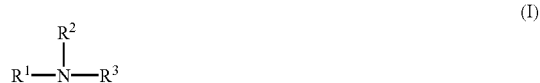

(I)

wherein each R group independently is $C_6$-$C_{10}$ arylene group, a straight or branched chain $C_2$-$C_8$ alkylene group optionally containing an arylene group, or a $C_4$-$C_{20}$ straight chain alkylene group containing one or more —NH— groups in the alkylene chain, each X is —O—, —S—, or —$NR^5$— where $R_5$ is hydrogen or $C_1$-$C_6$ alkyl, each AO group is independently ethyleneoxy, 1,2-propyleneoxy, or 1,2-butyleneoxy, n, m and p is from 1 to 50 and the sum of n, m and p is from 4 to 50, and the $R^4$ is independently —CH2-CH(OH)—$R^9$, wherein each $R^9$ independently represents a $C_4$-$C_{18}$ saturated or unsaturated, substituted or unsubstituted hydrocarbon group. The compound has surfactant and defoaming properties and is useful in latex paint, an ink, an adhesive, or a metal working compositions.

23 Claims, 2 Drawing Sheets

BRANCHED REACTION PRODUCTS

CROSS REFERENCE TO RELATED APPLICATIONS

This application claims the benefit of copending provisional application ser. No. 60/338,743, filed on Nov. 5, 2001, the entire contents of which are incorporated herein by reference.

FIELD OF THE INVENTION

This invention relates to surfactants and defoaming agents useful in both aqueous and nonaqueous compositions.

BACKGROUND OF THE INVENTION

Surface active foam control agents and detergency enhancement agents are widely used in both aqueous and nonaqueous compositions. However, these agents vary in their effectiveness and ecotoxicity, and new and more effective agents with low ecotoxicity are in constant demand.

SUMMARY OF THE INVENTION

The present invention relates to compounds useful as surfactants, and/or foam control agents, and/or rheology modifiers.

These compounds are compounds of formula I given below:

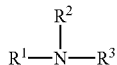
(I)

wherein $R^1$ and $R^2$ can be independently a substituted or unsubstituted, saturated or unsaturated $C_1$-$C_{36}$ hydrocarbon group, or a —RX(AO)$_n$—R$^4$ group in which R is a $C_6$-$C_{10}$ arylene group, a straight or branched chain $C_2$-$C_{20}$ alkylene group, optionally containing an arylene group, or a $C_4$-$C_{20}$ straight chain alkylene group containing one or more —NH— groups in the alkylene chain, X is —O—, —S—, or —NR$^5$— where $R^5$ is hydrogen or $C_1$-$C_6$ alkyl, each AO group is independently an ethyleneoxy (EO), a 1,2-propyleneoxy (PO), or a 1,2-butyleneoxy (BO) group, n is a number of from 1 to 100, and the $R^4$ group is a $C_1$-$C_{36}$ organic group; and the $R^3$ group is an —RX(AO)$_n$—R$^4$ group as defined above.

DETAILED DESCRIPTION

Figure 1:
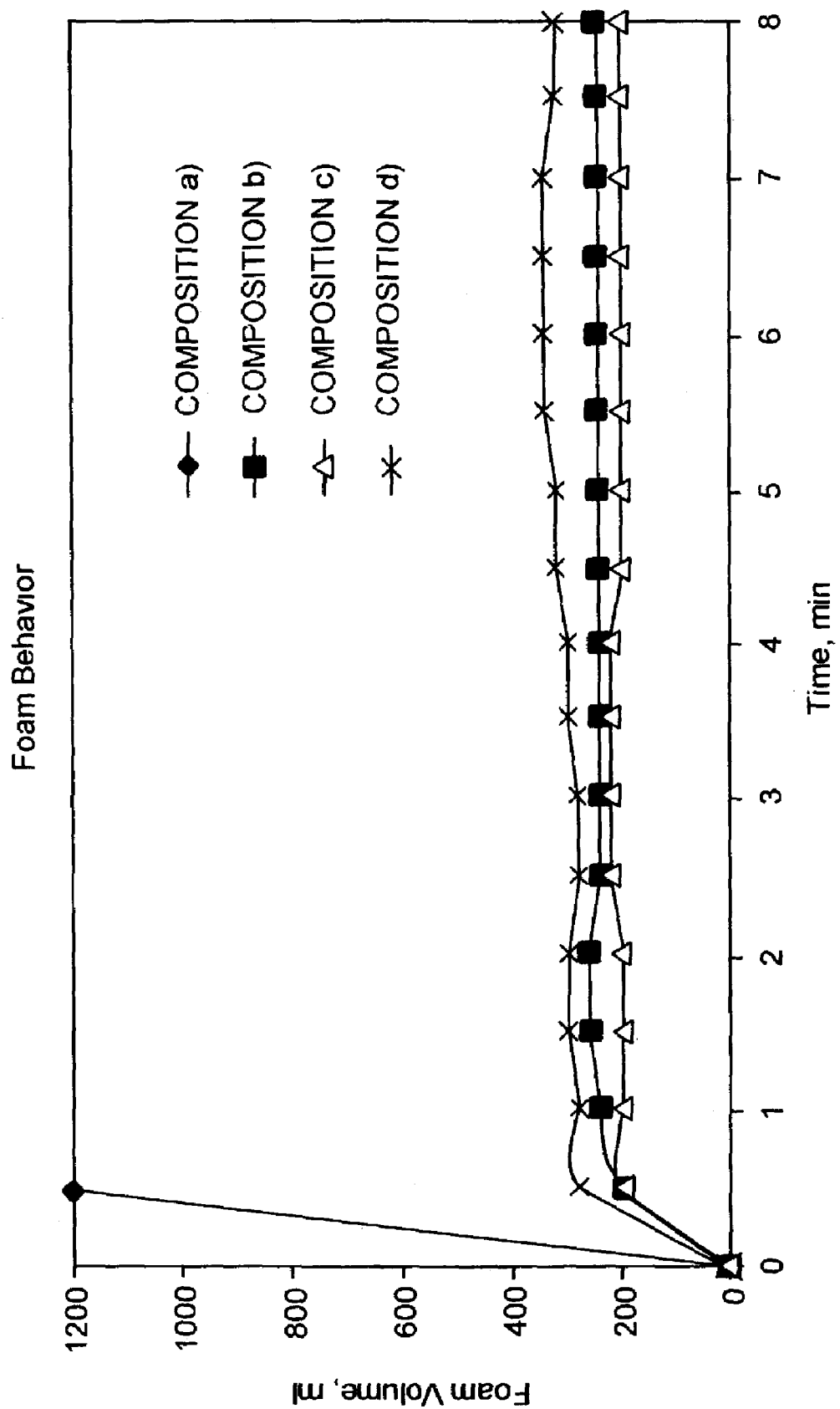
FIG. 1 is a graph showing the foam behavior of surfactants, including combinations thereof, in aqueous solutions.

Other than in the operating examples, or where otherwise indicated, all numbers expressing quantities of ingredients or reaction conditions used herein are to be understood as modified in all instances by the term "about".

In the compounds of formula I, when $R^1$ and/or $R^2$ are hydrocarbon groups, such groups include linear or branched alkyl groups having from 1 to 36 carbon atoms, preferably from 4 to 22 carbon atoms, more preferably from 4 to 12 carbon atoms, and most preferably from 8 to 10 carbon atoms; linear or branched alkenyl or alkynyl groups having from 2 to 36 carbon atoms, preferably from 4 to 22 carbon atoms, aryl groups having from 6 to 22 carbon atoms, e.g. phenyl, tolyl, xylyl, naphthyl, etc. and arenyl groups having from 7 to 36 carbon atoms. Arenyl groups are alkyl-substituted aromatic radicals having a free valence at an alkyl carbon atom, such as a benzylic group. These $R^1$ and/or $R^2$ groups can also be saturated carbocyclic groups, unsaturated carbocyclic groups having one or more multiple bonds, saturated heterocyclic groups, e.g. piperidino, morpholino, thiomorpholino, pyrrolidino, and the like, or unsaturated heterocyclic groups, such as the above groups having one or more multiple bonds. Any of the above groups can be substituted groups, i.e. the substituent groups can be single or multiple substituents such as a sulfur functionality, e.g. a mercaptan or thio group; a nitrogen functionality such as an amine or amide functionality; an alcohol functionality; a silicon functionality, e.g., a siloxane; an ether functionality, e.g. a $C_1$-$C_6$ alkoxy group; or any combination thereof.

With respect to the —RX(AO)$_n$—R$^4$ groups, the AO groups are preferably all ethyleneoxy groups, n is preferably a number of from 4 to 50, and the $R^4$ group can be

$C_{18}$ saturated or unsaturated, substituted or unsubstituted, hydrocarbon group, e.g. alkyl, alkenyl, cycloalkyl, arenyl, or aryl, optionally containing one or more of the substituents described above.

The compounds of the invention preferably have the following structure II:

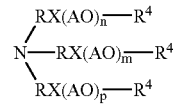
(II)

wherein R, X, AO, n, and $R^4$ have the meanings given in Formula I, and m and p are independently a number of from 1 to 100, provide that the sum of n, m, and p is from 3 to 100, preferably from 4 to 50. In the above Formula II, the AO groups are preferably at least mostly ethyleneoxy groups, and the $R^4$ groups are preferably all independently $C_1$-$C_{36}$ hydrocarbon groups.

More preferred compounds of the invention have the formula III below:

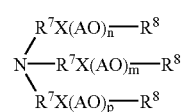
(III)

wherein $R^7$ is a straight or branched chain $C_2$-$C_{10}$ alkylene group, X has the meaning given in formula I, AO has the meaning given in formula I, but preferably all AO groups are ethyleneoxy groups, the sum of n, m, and p is from 6 to 27, preferably from 6 to 18, and more preferably from 6 to 12, and each $R^8$ group is independently a

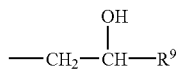

group in which $R^9$ is a $C_1$-$C_{18}$ straight or branched chain, saturated or unsaturated hydrocarbon group.

Even more preferred compounds of formula III are those in which the $R^7$ groups are all ethylene groups; the X groups are all —O—; the AO groups are all ethyleneoxy groups; n, m, and p total from 6 to 18, preferably from 6 to 12; and $R^9$ is a $C_4$-$C_{12}$ alkyl group.

The most preferred compound of the invention is the reaction product of (a) triethanolamine ethoxylated with an average of 9 moles of ethylene oxide and (b) about 3 moles of epoxylated 1-decene. The reaction mixture resulting therefrom will contain the following compound of formula IV:

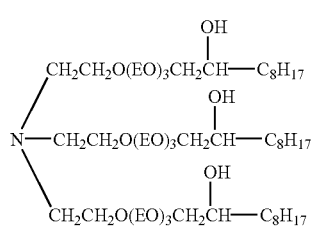

in which the 3 EO groups per chain represent an average of a total of 9 EO groups, and the $C_8H_{17}$ groups are straight or branched chain.

The compounds of formulae I, II, III, and IV can be prepared by (a) reacting a tertiary amine having at least one hydrogen atom which will react with an alkylene oxide, with a $C_2$-$C_4$ alkylene oxide, and (b) reacting the reaction product from step (a) with either (i) a $C_1$-$C_{36}$ organic halide, preferably a chloride or bromide, (ii) a $C_5$-$C_{20}$ epoxy compound or (iii) a $C_2$-$C_{19}$ carboxylic acid-based esterifying agent e.g.

where X is a halogen atom, or

where R' is a $C_1$-$C_6$ alkyl group and $R^6$ has the meaning given above.

Where the reactant in step (b) is a $C_5$-$C_{20}$ epoxy compound, the epoxy compound preferably has the formula

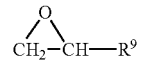

where $R^9$ has the meaning given above in formula III. However, epoxy compounds in which the epoxy group is not in the alpha position can also be used herein.

Reaction conditions for carrying out the above reactions will depend on the particular reactants employed and can be readily determined by those skilled in the art, especially since alkoxylation reactions, organic halide reactions, reactions with epoxy compounds, and esterification reactions are known reaction types.

When the X group in the above compounds of Formulas I, II, and III is —S— or —$NR^5$—, the amines in step (a) prior to alkoxylation containing an —SH or —$NR^5$H group can be readily prepared from the corresponding alcohols. For example, where X is —$NR^5$H, the corresponding alcohol can be subjected to a catalyzed ammoniation (with ammonia, or a lower alkylamine) for replacement of the hydroxyl, or to a capping of the hydroxyl with epichlorohydrin followed by ammoniation (with ammonia, or a lower alkylamine) of the resulting glycidal group. Where X is —SH, the corresponding alcohol can be converted to the mercaptan by methods well known to the art, e.g. by converting the alcohol to a halide and reacting the halide with sodium hydrosulfide.

The compounds of the invention can be used as surfactants and/or foam control agents and/or rheology modifying agents in both aqueous and nonaqueous compositions, and are particularly useful in minimizing or eliminating foaming in aqueous compositions containing high foaming surfactants, such as alkyl polyglycosides and anionic surfactants such as alcohol sulfates.

These reaction products can be used in aqueous cleaning compositions, in emulsion polymer latex compositions such as latex paints, in inks, in adhesives, in metal working compositions, and in other aqueous and nonaqueous compositions in which surfactants and/or defoaming agents and/or rheology modifying agents are advantageously present.

The reaction products of the invention are biodegradable, can act as surfactants, defoaming agents, and rheology modifying agents at the same time, contain no organic solvents, and do not adversely affect the detergency of other surfactants that may be present in compositions in which they are used since they are themselves surfactants. In addition, they do not contain any organically bound chlorine or other halides, i.e. they have a very low eco-toxicity.

The degree of hydrophilic and hydrophobic properties of the compounds of the invention can be readily controlled by controlling the type and number of alkyleneoxy groups and the carbon content of the hydrophobic groups. For example, the greater the number of ethyleneoxy groups present, the greater the water solubility, while the presence of 1,2-propyleneoxy groups and/or 1,2-butyleneoxy groups will decrease water solubility.

The compounds of the invention can be added to the above aqueous and nonaqueous compositions in a surfactant-effective and/or defoaming-effective quantity, and/or rheology modifying-effective quantity, usually from 0.01 to 20% by weight, preferably from 0.1 to 10% by weight, based on the weight of solids in the composition.

The compounds of the invention are particularly useful as a defoaming agent component of aqueous solutions containing one or more alkyl polyglycosides.

Alkyl polyglycosides are a class of nonionic surfactants that exhibit significantly higher foaming profiles than other nonionic surfactants, such as alcohol ethoxylates. In fact, it can be said that the foaming tendencies of alkyl polyglycosides more closely resemble those of anionic surfactants, such as alcohol sulfates, than the foaming tendencies of other nonionic surfactants. This higher foaming tendency makes the use of alkyl polyglycosides undesirable for many applications, e.g. cleaning-in-place for food processing plants, high pressure spray cleaning, bottle washing, floor cleaners and automatic dishwashing, wherein high levels of foam interfere with the cleaning and rinsing operation and reduce the efficiency of the operation.

A defoaming-effective amount is an amount effective to eliminate or decrease the foam generated by the alkyl polyglycoside as a result of some type of mechanical action such as mixing, pouring, and/or shaking. The amount required to eliminate and/or decrease foam will vary from one instance to another depending upon the nature of the alkyl polyglycoside surfactant or mixture of surfactants and the defoaming effect desired. A defoaming effective amount will be readily determinable by one of ordinary skill in the art. The defoaming effective amount will typically vary from a weight ratio of alkyl polyglycoside/defoamer of 4.0/1.0 to about 1.0/1.0.

Alkyl polyglycosides include those having formula IV below:

$$R_1O(R_2O)_b(Z)_a \quad \text{(IV)}$$

wherein $R_1$ is a monovalent organic radical having from 6 to 30 carbon atoms, preferably from 6 to 16 carbon atoms; $R_2$ is a divalent alkylene radical having from 2 to 4 carbon atoms; Z is a saccharide residue having 5 or 6 carbon atoms; b is a number having a value from 0 to 12; a is a number having a value from 1 to 6, preferably from 1.2 to 2.2, and more preferably from 1.4 to 1.7. Preferred alkyl polyglycosides which can be used in the compositions according to the invention have the formula I wherein Z is a glucose residue and b is zero. Such alkyl polyglycosides are commercially available, for example, as APG®, GLUCOPON®, or PLANTAREN® surfactants from Cognis Corporation, Ambler, Pa., 19002. Examples of such surfactants include but are not limited to:

1. GLUCOPON® 225 DK Surfactant—an alkyl polyglycoside in which the alkyl group contains 8 to 10 carbon atoms and having an average degree of polymerization of 1.7
2. GLUCOPON® 425N Surfactant—an alkyl polyglycoside in which the alkyl group contains 8 to 16 carbon atoms, having an average of 10.3 carbon atoms, and having an average degree of polymerization of 1.5.
3. GLUCOPON® 625 UP Surfactant—an alkyl polyglycoside in which the alkyl group contains 12 to 16 carbon atoms and having an average degree of polymerization of 1.6.
4. APG® 325N Surfactant—an alkyl polyglycoside in which the alkyl group contain 9 to 11 carbon atoms and having an average degree of polymerization of 1.5.
5. GLUCOPON® 600UP Surfactant—an alkyl polyglycoside in which the alkyl group contains 12 to 16 carbon atoms and having an average degree of polymerization of 1.4.
6. PLANTAEREN® 2000 Surfactant—a $C_8$-$C_{16}$ alkyl polyglycoside in which the alkyl group contains 8 to 16 carbon atoms and having an average degree of polymerization of 1.5.
7. PLANTAEREN® 1300 Surfactant—a $C_{12}$-$C_{16}$ alkyl polyglycoside in which the alkyl group contains 12 to 16 carbon atoms and having an average degree of polymerization of 1.6.
8. GLUCOPON® 220N Surfactant—an alkyl polyglycoside in which the alkyl group contains 8 to 10 carbon atoms and having an average degree of polymerization of 1.5.

Other examples include alkyl polyglycoside surfactant compositions which are comprised of mixtures of compounds of formula I wherein Z represents a moiety derived from a reducing saccharide containing 5 or 6 carbon atoms; a is a number having a value from 1 to about 6; b is zero; and $R_1$ is an alkyl radical having from 8 to 20 carbon atoms. The compositions are characterized in that they have increased surfactant properties and an HLB in the range of about 10 to about 16 and a non-Flory distribution of glycosides, which is comprised of a mixture of an alkyl monoglycoside and a mixture of alkyl polyglycosides having varying degrees of polymerization of 2 and higher in progressively decreasing amounts, in which the amount by weight of polyglycoside having a degree of polymerization of 2 or mixtures thereof with the polyglycoside having a degree of polymerization of 3 predominate in relation to the amount of monoglycoside, said composition having an average degree of polymerization of about 1.8 to about 3. Such compositions, also known as peaked alkyl polyglycosides, can be prepared by separation of the monoglycoside from the original reaction mixture of alkyl monoglycoside and alkyl polyglycosides after removal of the alcohol. This separation may be carried out by molecular distillation and normally results in the removal of about 70-95% by weight of the alkyl monoglycosides. After removal of the alkyl monoglycosides, the relative distribution of the various components, mono- and polyglycosides, in the resulting product changes and the concentration in the product of the polyglycosides relative to the monoglycoside increases as well as the concentration of individual polyglycosides to the total, i.e. DP2 and DP3 fractions in relation to the sum of all DP fractions. Such compositions are disclosed in U.S. Pat. No. 5,266,690, the entire contents of which are incorporated herein by reference.

This invention will be illustrated but not limited by the following examples.

EXAMPLES

Example 1

Synthesis of POE(9) triethanolamine tris (2-hydroxydecyl) ether.

Into a 500 ml 4-neck flask fitted with a cold trap was placed 100 g. of POE(9) triethanolamine (triethanolamine ethoxylated with 9 moles of ethylene oxide) under nitrogen. The flask was heated to 150° C. with agitation and nitrogen sparge to drive off any moisture. Then 100 g. of 1,2-epoxydecane was added dropwise at 150° C., and the resulting reaction mixture was heated at 150° C. for 3.5 hours. The flask was then subjected to vacuum to remove any unreacted epoxide. No epoxide was seen in the cold trap. The reaction mixture was then cooled to 90° C. and 0.8 g. of 30% hydrogen peroxide was added with agitation for 45 minutes to bleach the product.

Example 2

The following 4% active aqueous surfactant compositions were prepared by dissolving the non-aqueous components in water:

| Components | % by weight | Active Ratio GLUCOPON ® 425N: additive |
|---|---|---|
| a) DI WATER | 92.0 | 1:0 |
| GLUCOPON ® 425N | 8.0 | |
| b) DI WATER | 92.59 | 5.75:1 |
| GLUCOCPN ® 425N | 6.82 | |
| 9TTE[1] | 0.59 | |
| c) DI WATER | 92.73 | 4.5:1 |
| GLUCOPON ® 425N | 6.55 | |
| 9TTE | 0.72 | |
| d) DI WATER | 92.73 | 4.5:1 |
| GLUCOPON ® 425N | 6.55 | |
| DEHYPOUND ® ST-15[2] | 0.72 | |

[1]-9TTW is POE(9) triethanolamine tris-(2-hydroxydecyl) ether prepared in Example 1.
[2]-DEHYPOUND ® ST-15 is a commercial highly effective foam control agent produced by the base-catalyzed reaction between epichlorohydrin and n-octyl/n-decyl (45:55) alcohol · 4EO (mole ratio 1:0.65).

The above surfactant compositions were further diluted by adding 10 grams of the composition to 400 grams of soft water, resulting in 0.1% total active solutions. The 0.1% active solutions were transferred to a dynamic foam cell and circulated for a total of 8 minutes. The foam cell consisted of a 2-liter jacketed graduate, peristaltic pump with variable voltage controller, and silicone and glass tubing. The test mixture was circulated at a constant temperature and flow rate; and fell from a constant height of 30 cm back into itself, creating foam. The tests were run under the following set of conditions: a 0.1% active solution of the test surfactant in soft (10-15 ppm) water was circulated at 25° C. and the foam volume was read every 30 seconds.

The results obtained are set forth in Table 1 below:

TABLE 1

FOAM VOLUMES

| Time min. | COM-POSITION a) | COM-POSITION b) | COM-POSITION c) | COM-POSITION d) |
|---|---|---|---|---|
| 0 | 0 | 0 | 0 | 0 |
| 0.5 | 1200 | 200 | 200 | 280 |
| 1 | | 240 | 200 | 280 |
| 1.5 | | 260 | 200 | 300 |
| 2 | | 260 | 200 | 300 |
| 2.5 | | 240 | 220 | 280 |
| 3 | | 240 | 220 | 280 |
| 3.5 | | 240 | 220 | 300 |
| 4 | | 240 | 220 | 300 |
| 4.5 | | 240 | 200 | 320 |
| 5 | | 240 | 200 | 320 |
| 5.5 | | 240 | 200 | 340 |
| 6 | | 240 | 200 | 340 |
| 6.5 | | 240 | 200 | 340 |
| 7 | | 240 | 200 | 340 |
| 7.5 | | 240 | 200 | 320 |
| 8 | | 240 | 200 | 320 |

The above results have been plotted in graph form in FIG. 1.

It should be noted that the compound of Example 1 is a more effective foam control agent than the commercial product DEHYPOUND® ST-15 since 1 part of DEHYPOUND® ST-15 for every 4.5 parts of actives in GLUCOPO® 425N is required to obtain satisfactory foam control, while only 1 part of the compound of Example 1 is needed for every 5.75 parts of actives in GLUCOPON® 425N to achieve even better foam control results.

Example 3

The aqueous surfactant compositions prepared in Example 2, diluted 1% total actives, were tested for hard surface detergency according to the following procedure:

The test soil used had the following composition:

| Composition | Parts by weight |
|---|---|
| Kerosene | 55 |
| Mineral Oil | 6 |
| Vegetable Oil | 8 |
| Carbon Black | 1.5 |
| Bandy Black Clay | 25 |

0.4 ml of the above test soil was applied to the rough side of 3"×3" Armstrong 56830 Chalk II vinyl composite tiles. The soil was spread with the grain in the panel, using a nylon brush. An additional 0.1 ml of soil was then added to the tile and spread as above. The panels were dried for 20 minutes at room temperature, then for 20 minutes at 100° C., and finally for 20 minutes at room temperature.

The cleaning operation was carried out as follows, after first measuring the reflectance of the soiled tiles:

1. Two soiled test panels were placed in a Gardner Apparatus wash tray, with the "grain" parallel to the direction of sponge travel.
2. 200 ml of test solution were added to the wash tray, and left for one minute.
3. The test panels were scrubbed with a synthetic sponge for 16 cycles, rotating panels 90° after 8 cycles. The total number of cycles can be varied from 8 to 40, provided the same number is used for each test solution.
4. The panels were rinsed with DI water and dried at room temperature for at least one hour.
5. Steps 1-4 were repeated for a total of four panels for each test solution.

The reflectance of the washed panels were measured after the drying period, and averaged for each test solution.

Calculation:

$$\% \text{ Soil Removal} = \frac{\{Rw - Rs\} \times 100}{\{Ru - Rs\}}$$

Figure 2:
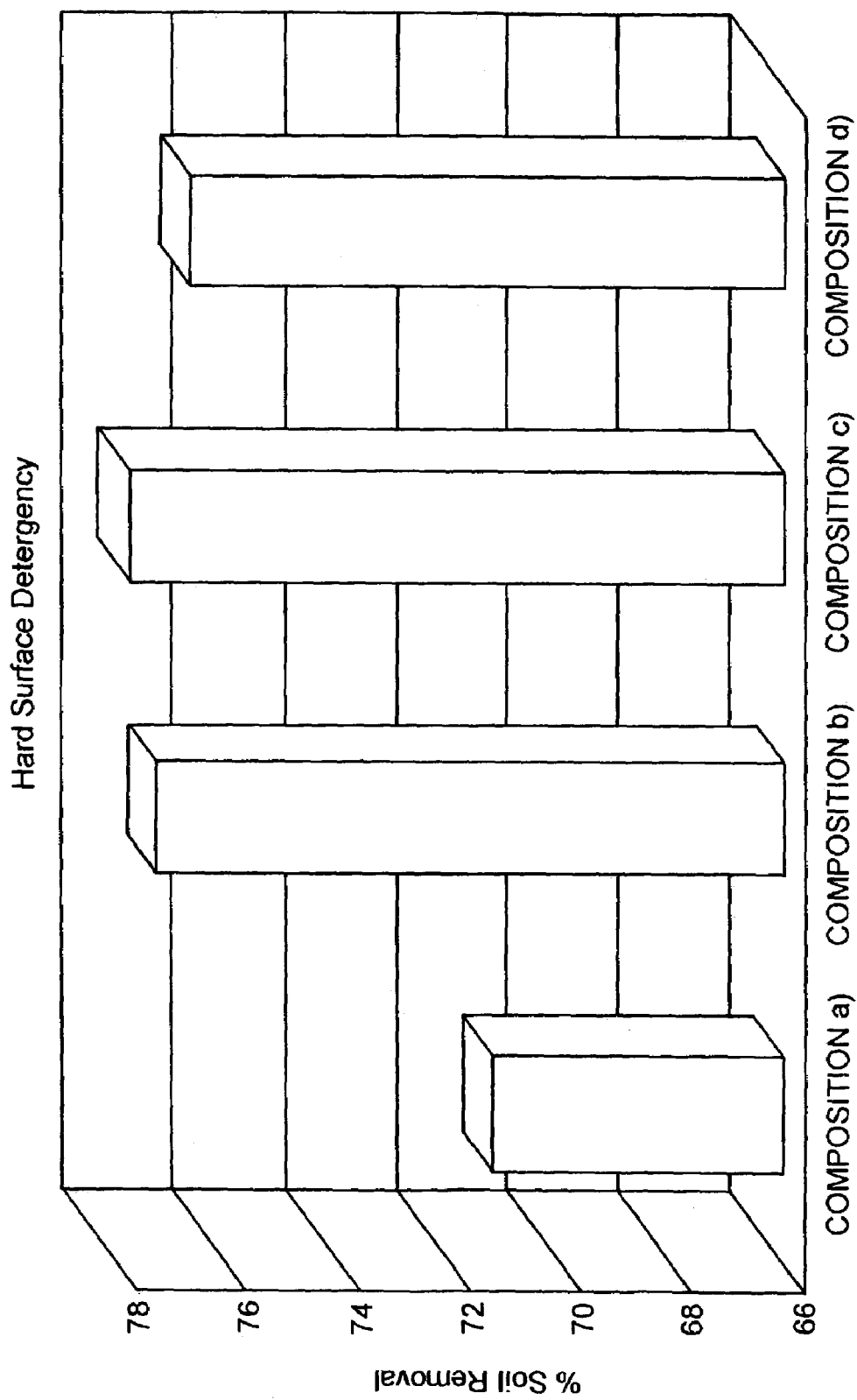
FIG. 2 is a graph showing the % soil removal obtained by the aqueous surfactant solutions of FIG. 1.

Rw = Reflectance of washed panel
Rs = Reflectance of soiled panels
Ru = Reflectance of unsoiled panels The results obtained are set forth in Table 2 below, and shown in graph form in FIG. 2.

TABLE 2

| | % of soil removal | | |
|---|---|---|---|
| Composition a) | Composition b) | Compositions c) | Composition d) |
| 71.2 | 77.2 | 77.7 | 76.6 |

It can be seen from the above table that the compositions containing the compounds of the invention (compositions b) and c)) are more effective hard surface detergents than both GLUCOPON® 425N alone (composition a)), and composition d) containing DEHYPOUND® ST-15 even though DEHYPOUND® ST-15 is present in composition d) in greater quantity than the compound of Example 1 in compositions b) and c).

What is claimed is:

1. A compound of formula:

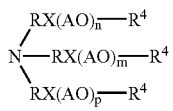

(II)

wherein each R group independently represents a $C_6$-$C_{10}$ arylene group, a straight or branched chain $C_2$-$C_{20}$ alkylene group optionally containing an arylene group, or a $C_4$-$C_{20}$ straight chain alkylene group containing one or more —NH— groups in the alkylene chain, each X is —O—, —S—, or —$NR^5$— where $R_5$ is hydrogen or $C_1$-$C_6$ alkyl, each AO group is independently an ethyleneoxy (EO), a 1,2-propyleneoxy (PO), or a 1,2-butyleneoxy (BO) group, n, m and p is a number of from 1 to 50 and the sum of n, m and p is from 4 to 50, and the $R^4$ group independently represents a moiety selected from the group consisting of —CH2—OH(OH)—$R^9$ group, wherein each $R^9$ independently represents a $C_4$-$C_{18}$ saturated or unsaturated, substituted or unsubstituted hydrocarbon group.

2. The compound according to claim 1, wherein each $R^9$ independently represents a $C_4$-$C_{12}$ alkyl group.

3. The compound according to claim 1, wherein the sum of n, m and p is from 6 to 27.

4. The compound of claim 3, wherein the sum of n, m and p is from 6 to 12.

5. A compound of the general formula (III):

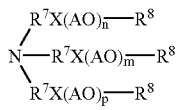

(III)

wherein each $R^7$ independently represents a straight or branched chain $C_2$-$C_{20}$ alkylene group, each X independently represents —O—, —S—, or —$NR^5$— where $R_5$ is hydrogen or $C_1$-$C_6$ alkyl, each AO group is independently an ethyleneoxy (EO), a 1,2-propyleneoxy (PO), or a 1,2-butyleneoxy (BO) group, the sum of n, m and p is from 6 to 27, and each $R^8$ group is independently a —CH2—CH(OH)—$R^9$ group in which $R^9$ is a $C_4$-$C_{18}$ straight or branched chain, saturated or unsaturated hydrocarbon group.

6. The compound according to claim 5, wherein each AO group represents an ethyleneoxy group.

7. The compound according to claim 5, wherein each X represents an —O—.

8. The compound according to claim 5, wherein the $R^7$ groups are all ethylene groups, the X groups are all —O— groups, and the sum of n, m and p is from 6 to 18.

9. The compound according to claim 8, wherein each AO group represents an ethyleneoxy group.

10. The compound according to claim 8, wherein all $R^9$ groups are $C_4$-$C_{12}$ alkyl groups, the sum of n, m and p is from 6 to 12, and all AO groups are ethyleneoxy groups.

11. The compound of claim 5, wherein all $R^9$ groups are $C_4$-$C_{12}$ alkyl groups.

12. The compound of claim 5, wherein the sum of n, m and p is from 6 to 12.

13. An aqueous or nonaqueous composition containing a surfactant-effective quantity of at least one compound according to claim 5.

14. The composition according to claim 13, wherein the composition is a latex paint, an ink, an adhesive, or a metal working composition.

15. An aqueous or nonaqueous composition containing a defoaming-effective quantity of at least one compound according to claim 5.

16. The composition according to claim 15, wherein the composition is a latex paint, an ink, an adhesive, or a metal working composition.

17. A compound of the general formula IV:

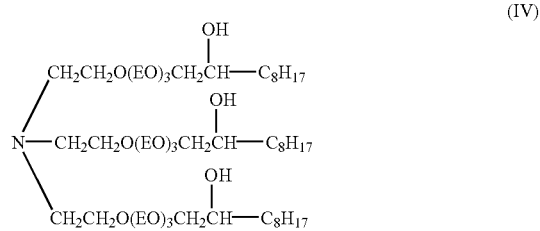

(IV)

in which EO is ethyleneoxy, the 3 EO groups per chain represent an average of the total of 9 EO groups, and the $C_8H_{17}$ groups are straight or branched chain.

18. An aqueous or nonaqueous composition containing a surfactant-effective quantity of at least one compound according to claim 17.

19. The composition according to claim 18, wherein the composition is a latex paint, an ink, an adhesive, or a metal working composition.

20. An aqueous or nonaqueous composition containing a defoaming-effective quantity of at least one compound according to claim 17.

21. The composition according to claim 20, wherein the composition is a latex paint, an ink, an adhesive, or a metal working composition.

22. A reaction product of triethanolamine ethoxylated with 9 moles of ethylene oxide and an epoxylated $C_{10}$ olefin, wherein the ethoxylated triethanolamine and the epoxylated olefin are reacted in a molar ratio of about 1:3.

23. The reaction product according to claim 22, wherein the $C_{10}$ olefin is an alpha olefin.

* * * * *